US010478342B2

(12) United States Patent
Dick et al.

(10) Patent No.: US 10,478,342 B2
(45) Date of Patent: Nov. 19, 2019

(54) OPHTHALMOLOGIC LASER DEVICE AND METHOD FOR PREVENTING AND TREATING AFTERCATARACT

(75) Inventors: Manfred Dick, Gefell (DE); Juergen Kuehnert, Jena (DE); Matthias Reich, Jena (DE)

(73) Assignee: CARL ZEISS MEDITEC AG, Jena (DE)

( * ) Notice: Subject to any disclaimer, the term of this patent is extended or adjusted under 35 U.S.C. 154(b) by 373 days.

(21) Appl. No.: 14/235,810

(22) PCT Filed: Jul. 26, 2012

(86) PCT No.: PCT/EP2012/064650
§ 371 (c)(1),
(2), (4) Date: Jan. 29, 2014

(87) PCT Pub. No.: WO2013/017513
PCT Pub. Date: Feb. 7, 2013

(65) Prior Publication Data
US 2014/0194860 A1    Jul. 10, 2014

(30) Foreign Application Priority Data
Jul. 29, 2011   (DE) .................. 10 2011 109 058

(51) Int. Cl.
*A61F 9/008*   (2006.01)

(52) U.S. Cl.
CPC ........ *A61F 9/0084* (2013.01); *A61F 9/00825* (2013.01); *A61F 2009/0087* (2013.01);
(Continued)

(58) Field of Classification Search
CPC .... A61F 2009/0087; A61F 2009/00889; A61F 2009/00887; A61F 2009/00851;
(Continued)

(56) References Cited

U.S. PATENT DOCUMENTS 5,733,276 A   3/1998 Belkin
6,623,477 B1   9/2003 Elbrecht et al.
(Continued)

FOREIGN PATENT DOCUMENTS

IN   01996MU2006 A   12/2006
WO   WO 0027325 A1   5/2000
(Continued)

OTHER PUBLICATIONS

Wolfram Wehner, et al., "Prevention of lens capsule opacification with ARC neodymium, YAG laser photolysis after phaceomulsification", Dec. 2010, Elsevier, USA.

*Primary Examiner* — Carl H Layno
*Assistant Examiner* — Dacheng Xie
(74) *Attorney, Agent, or Firm* — Leydig, Voit & Mayer, Ltd.

(57) ABSTRACT

An ophthalmologic laser device includes a pulsed laser configured to produce radiation focused along at treatment beam path. A variably adjustable beam deflector unit and a focusing lens system are disposed in the treatment beam path. The deflector unit is configured to focus the radiation in different target volumes. Measuring equipment is configured to determine a shape and position of optical interfaces along a detection beam path. A control unit is configured to control the laser and the deflector unit and to implement steps including determining a shape and position of an interface of a membrane of a capsular bag of an eye located in a treatment area using the measuring equipment, determining coordinates of a target volume such that, on irradiation of the target volume, a pressure wave runs from the target volume to the anterior or posterior membrane, and adjusting the deflector unit to the target determined volume.

8 Claims, 11 Drawing Sheets

(52) U.S. Cl.
CPC ............ *A61F 2009/00846* (2013.01); *A61F 2009/00853* (2013.01); *A61F 2009/00872* (2013.01); *A61F 2009/00887* (2013.01); *A61F 2009/00889* (2013.01)

(58) Field of Classification Search
CPC .................. A61F 9/008; A61F 9/00754; A61F 2009/00844; A61F 9/00736; A61F 9/00802; A61B 3/102; A61B 18/20; A61B 3/107
USPC ........................................................ 606/2–19
See application file for complete search history.

(56) References Cited

U.S. PATENT DOCUMENTS

| | | | |
|---|---|---|---|
| 6,726,679 B1 | 4/2004 | Dick | |
| 2002/0103478 A1 | 8/2002 | Gwon et al. | |
| 2004/0243111 A1 | 12/2004 | Bendett et al. | |
| 2005/0165387 A1 | 7/2005 | Lubatschowski et al. | |
| 2006/0155265 A1 | 7/2006 | Juhasz et al. | |
| 2006/0195076 A1* | 8/2006 | Blumenkranz | A61F 9/00736 606/4 |
| 2007/0027539 A1 | 2/2007 | Pynson | |
| 2009/0076602 A1 | 3/2009 | Ho et al. | |
| 2009/0080739 A1* | 3/2009 | Rogers | A61B 3/102 382/131 |
| 2009/0137993 A1* | 5/2009 | Kurtz | A61F 9/00736 606/6 |
| 2010/0004641 A1* | 1/2010 | Frey | A61F 9/008 606/4 |
| 2010/0022995 A1* | 1/2010 | Frey | A61F 9/008 606/4 |
| 2010/0191230 A1 | 7/2010 | Dick et al. | |
| 2010/0292678 A1* | 11/2010 | Frey | A61F 9/008 606/5 |
| 2011/0172649 A1* | 7/2011 | Schuele | A61F 9/008 606/4 |
| 2011/0264081 A1 | 10/2011 | Reich et al. | |

FOREIGN PATENT DOCUMENTS

| | | |
|---|---|---|
| WO | WO 0113838 A1 | 3/2001 |
| WO | WO 2004105661 A1 | 12/2004 |
| WO | WO 2005070358 A1 | 8/2005 |
| WO | WO 2007084694 A2 | 7/2007 |
| WO | WO 2009039309 A2 | 3/2009 |
| WO | WO 2009059251 A2 | 5/2009 |
| WO | WO 2009146906 A2 | 12/2009 |

* cited by examiner

OPHTHALMOLOGIC LASER DEVICE AND METHOD FOR PREVENTING AND TREATING AFTERCATARACT

CROSS REFERENCE TO RELATED APPLICATIONS

This application is a U.S. National Phase application under 35 U.S.C. § 371 of International Application No. PCT/EP2012/064650, filed on Jul. 26, 2012, and claims benefit to German Patent Application No. DE 10 2011 109 058.8, filed on Jul. 29, 2011. The International Application was published in German on Feb. 7, 2013 as WO 2013/017513 A2 under PCT Article 21 (2).

FIELD

The invention relates to an ophthalmologic laser device having at least one short pulse or one ultra-short pulse laser, the radiation of which can be focussed along a treatment beam path, which comprises a variably adjustable beam deflector unit and a focussing lens system, within a treatment area in different target volumes by means of the deflector unit, and measuring equipment for determination of the shape and position of optical interfaces along a detection beam path, as well as a control unit for controlling the laser and the deflector unit, and to methods for the prophylaxis of aftercataract during or after a cataract operation or for the treatment of aftercataract following a cataract operation.

The measuring equipment in this context is disposed in a detection beam path and serves to measure interfaces which are disposed in the detection beam path and in particular in the part of the treatment beam path disposed behind the focussing lens system from the direction of the laser. An ultra-short pulse laser is constructed for emission of pulses having a duration of the order of femtoseconds or picoseconds. A short pulse laser, on the other hand, is constructed for emission of pulses having a duration of the order of nanoseconds.

The invention moreover relates to a fixing device for an eye, comprising a suction device and a disc for transmission of laser radiation, wherein the suction device surrounds the disc. The suction device is suitable for fixing the eye relative to the disc and therefore also relative to a focussing lens system of a laser device by means of reduced pressure. The suction device is typically disposed in a circular manner around the disc. The disc itself can be flat or curved concavely on the eye side, in particular with a physiological curvature. On the laser side the disc is typically flat.

BACKGROUND

In the prior art, ophthalmologic laser devices are used in all areas of the eye. For example, in laser-assisted intrastromal keratomileusis (LASIK), with the aid of a microkeratome a stromal flap having a thickness of approx. 160 µm is detached from the cornea and folded open. The material-removing laser treatment is then performed in the intrastromal tissue thereby exposed, and after the treatment the flap is folded closed. With this procedure, patients have minimal pain and a rapid recovery of sight after the operation. Alternatively, the material-removing laser treatment can be carried out in a photorefractive keratectomy (PRK) on the stromal surface, after the upper epithelial layer, which is about 50 µm thick, has been irreversibly removed from the Bowman membrane with hockey knives. In both cases, an ArF excimer laser is used for refractive correction of the cornea by ablation of tissue.

In addition, femtosecond lasers have recently been used to make incisions in the cornea (femto-LASIK). Such apparatuses are also called laser microkeratomes. In this context, photodisruption is generated in the target volume, leading to a minimal blistering in the stromal tissue. If a target spot is placed on a target spot by means of a scanner system, any desired incisions (perforations) can be introduced into the cornea. Such incisions are also called laser incisions in the following. It is known from US 2006/0155265 A1, for example, to cut the flap by means of a femtosecond laser system. The ablation of the stromal tissue required for refractive correction is then carried out in a known manner by means of an excimer laser, so that mechanical manipulation can be omitted completely. However, two laser systems are necessary.

WO 2004/105661 A1 describes using the fs laser to cut an intrastromal lenticule, which can be removed, for example, through relatively small openings with the aid of suitable tweezers or also cannulas, in order to modify the refractive properties of the cornea. Furthermore, intrastromal pockets can be prepared by this method, into which artificial inlays can be introduced for refractive correction.

What is known as laser photocoagulation is performed in the fundus of the eye for various diseases of the retina, for example detached retina. As a rule, lasers emitting continuous waves (cw) are used for this purpose. The main field of application of photocoagulation is for focussing the metabolism on the still healthy regions of the retina by obliterating diseased tissue. Photocoagulation may moreover stimulate biochemical cofactors. In the case of holes in the macula or the onset of retinal detachment, scar formation can be used to fasten the retina to the layer of the eyeball lying underneath it, the choroid membrane.

In addition to refractive correction of the cornea by laser surgery and to laser coagulation, there are laser-assisted methods for therapy of the eye lens. For example, WO 01/13838 A1 and WO 2005/070358 A1 describe the treatment of presbyopia by means of fs lasers. In this, the hardened lens is restored by suitable laser incisions or photodisruption blister fields to a state of better deformability by the capsular bag or the ciliary muscle. In principle the accommodative capacity of the lens can thus be partially regenerated.

In cataract surgery, i.e. the replacement of the clouded eye lens by an artificial intraocular lens (IOL), what is known as phacoemulsification is established as a standard method for complete removal of the pathologically cloudy lens. In this context, the capsular bag surrounding the lens and comprising an anterior and a posterior membrane is cut open (capulorhexis) from the front (anterior). The lens is then emulsified with the aid of an ultrasonic handpiece to be introduced into the lens and moved in the lens, in order subsequently to be able to remove the lens material by suction. Methods based on Er:YAG and Nd:YAG lasers are also known, for example from WO 00/27325 A1, wherein the lens is broken up with the aid of low-frequency (10-100 Hz) laser ablations or laser-induced acoustic shock waves into segments which are easier to remove by suction These ultrasound or laser methods are invasive and can only be used during a conventional surgical intervention on the opened eye.

Significantly less invasive is a method which is described, for example, in WO 2009/059251 A2, wherein both the capsulorhexis incision opening up the anterior of the capsular bag and the fragmentation of the lens are carried out by means of an fs laser navigated by means of optical coherence tomography. In the method described in US 2009/137993 A, the access opening in the cornea is additionally also cut by means of the fs laser.

What is known as aftercataract typically occurs as a side effect of cataract surgery. It is a posterior capsule opacity (PCO), which develops after a cataract operation due to a proliferation of epithelial cells remaining in the capsular bag (lens epithelial cell, LEC). For treatment of aftercataract, what is known as aftercataract capsulotomy with a Q-switched Nd:YAG laser has hitherto been the method of choice. In this case, the laser beam is focussed behind the posterior capsular bag membrane and photodisruption is generated, the pressure wave of which tears the posterior capsular bag peripherally. The optically cloudy posterior membrane is removed from the optical zone of the eye by several shots, so that the patient's vision is no longer impaired.

This destruction of the posterior capsular bag membrane can be accepted with many standard IOLs, but involves risks: In view of the mechanical stability of the eye, prolapse of the vitreous body may occur due to the destroyed capsular bag; the pressure waves during a posterior YAG laser capsulotomy may increase the probability of retinal detachment.

In view of new approaches to cataract surgery, for example the refilling of the lens capsule with gelatinous synthetic lens material described inter alia in US 2009/076602 A1, in order to re-establish a certain accommodation of the eye, an intact capsular bag is required. Posterior capsulotomy is a disadvantage in this respect. Aftercataract capsulotomy can moreover present problems because the laser radiation is applied through the implanted IOL, which may thereby become damaged. There are therefore different approaches for preventing the development of aftercataract.

One possibility for preventing aftercataract is known in particular from paediatric surgery and involves the surgical opening of the posterior capsular bag membrane. The surgical intervention is carried out from the vitreous body chamber in connection with a (at least partial) pars plana vitrectomy and is therefore too involved and associated with too many complications for normal cataract operations. In particular, the reduced stability of an opened posterior capsular bag membrane can lead to a vitreous body prolapse.

To prevent aftercataract it is moreover known, for example from IN 01996MU2006 A, to kill or suppress the growth of LECs medicinally. This can be effected, for example, by flushing the capsular bag during cataract surgery. The outlay for flushing or for introduction of the medicaments is a disadvantage in this case. An addition or alternative to this are specially shaped intraocular lenses with sharp edges, which likewise impede the growth of the epithelial cells. Such IOLs are described, for example, in US 2007/027539 A1. The limitations in designing the lens shape due to the specified sharp edges are a disadvantage of this.

A further known possibility for prophylaxis of aftercataract is to generate shock waves intraoperatively, after removal of the old lens body and before insertion of a replacement lens, by means of a metal body to be inserted into the capsular bag and irradiated with an Nd:YAG laser. In this context the beam guide equipment for the laser radiation, like the metal body, must be inserted in the form of a probe into the eye and into the capsular bag and placed manually in the immediate vicinity in front of the epithelial cell layer. The shock waves lead to a detachment of the LEC layer from the capsular bag, so that the epithelial cells can be removed by suction. The probability of the occurrence of PCO thereby decreases. As a disadvantage, however, this method requires a separate work step, which must be performed manually with great care and skill, and additional equipment.

SUMMARY

In an embodiment, the present invention provides an ophthalmologic laser device including a pulsed laser configured to produce radiation focused along at treatment beam path. A variably adjustable beam deflector unit and a focusing lens system are disposed in the treatment beam path. The deflector unit is configured to focus the radiation in different target volumes. Measuring equipment is configured to determine a shape and position of optical interfaces along a detection beam path. A control unit is configured to control the laser and the deflector unit and to implement steps including determining a shape and position of at least one interface of a membrane of a capsular bag of an eye located in a treatment area using the measuring equipment, determining coordinates of a target volume such that, on irradiation of the target volume with a laser pulse of predetermined pulse energy, a pressure wave runs from the target volume at least up to the anterior or posterior membrane without tearing the respective membrane, and adjusting the deflector unit to the target determined volume so as to irradiate the target volume with at least one laser pulse of the predetermined pulse energy using the laser.

In an embodiment, the present invention also provides an ophthalmologic laser device including an ultra-short pulse laser configured to produce radiation focused along a treatment beam path. A variably adjustable beam deflector unit and a focusing lens system are disposed in the treatment beam path. The deflector unit is configured to focus the radiation in different target volumes. Measuring equipment is configured to determine a shape and position of optical interfaces along a detection beam path. A control unit is configured to control the laser and the deflector unit and to implement steps including determining a shape and position of at least one interface of an anterior membrane of a capsular bag of an eye located in a treatment area using the measuring equipment, determining coordinates of several target volumes where each target volume lies at least partially in the anterior membrane such that, on irradiation of the target volume with a laser pulse of predetermined pulse energy, a border of a region of the anterior membrane is perforated photodisruptively, where the region lies away from a visual axis penetration zone of the anterior membrane, and adjusting the deflector unit, respectively, to each determined target volume so as to irradiate the respective target volume with at least one laser pulse of the predetermined pulse energy using the laser.

In another embodiment, the present invention provides an ophthalmologic laser device including an ultra-short pulse laser configured to produce radiation focused along a treatment beam path. A variably adjustable beam deflector unit and a focusing lens system are disposed in the treatment beam path. The deflector unit is configured to focus the radiation in different target volumes. Measuring equipment is configured to determine a shape and position of optical interfaces along a detection beam path. A control unit is configured to control the laser and the deflector unit and to implement steps including determining a shape and position of at least one interface of an posterior membrane of a capsular bag of an eye located in a treatment area using the measuring equipment, determining coordinates of several target volumes where each target volume lies at least partially in the posterior membrane such that, on irradiation of the target volume with a laser pulse of predetermined pulse energy, a border of a region of the posterior membrane is perforated photodisruptively, where the region border lies around a visual axis penetration zone of the posterior membrane, and adjusting the deflector unit, respectively, to each determined target volume so as to irradiate the target volume with at least one laser pulse of the predetermined pulse energy using the laser

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

In all the drawings, corresponding parts carry the same reference symbols.

DETAILED DESCRIPTION

Figure 1A:
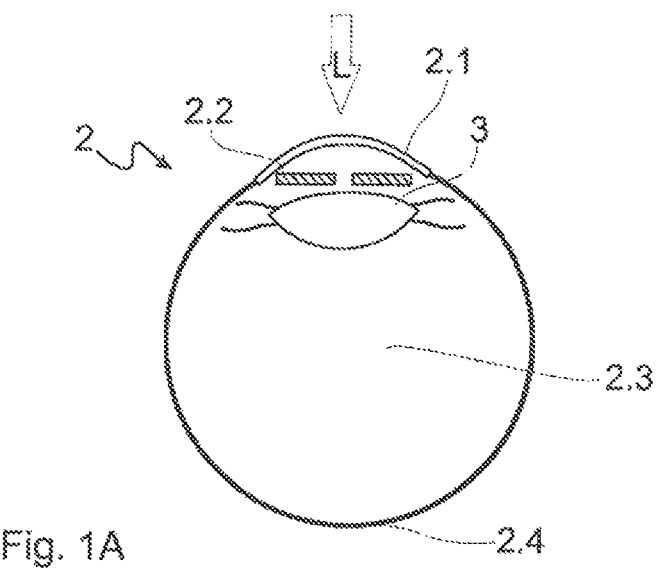
FIG. 1 shows the structure of the human eye, in particular the eye lens.

In an embodiment, the present invention provides methods and ophthalmologic laser devices of the type mentioned at the outset which make possible the prophylaxis and/or treatment of PCO with a lower outlay, in particular with a lower time outlay. In addition, a fixing device of the type mentioned at the outset is to be provided which makes possible an aftercataract prophylaxis with a lower outlay.

According to embodiments of the invention, for an ophthalmologic laser device of the type mentioned at the outset, it is envisaged to configure the control unit to implement the following steps:
  determination of the shape and position of at least one interface of a capsular bag of an eye located in the treatment area by means of the measuring equipment,
  determination of the coordinates of a target volume relative to the at least one interface,
  adjustment of the deflector unit to the target volume determined (so that the beam runs through the coordinates thereof) and irradiation of the target volume with at least one laser pulse by means of the laser. The target volume can also be irradiated with several laser pulses.

A laser device constructed in such a manner makes possible automatic measurement of the characteristic interface(s) and, as a result, irradiation is performed automatically as prophylaxis or treatment of PCO, for example by a short pulse laser capsulotomy, which is known per se, of the posterior capsular bag membrane, with a lower outlay, in particular with a lower time outlay, than in the prior art by determining the irradiated target volume relative to the characteristic interface(s).

Possible interface(s) to be measured are, for example, the interfaces of the anterior and the posterior membrane of the capsular bag. In this context, the anterior membrane is that part of the capsular bag facing the cornea. The posterior membrane is that part of the capsular bag facing the retina. The area of the capsular bag in which the anterior and the posterior membrane are joined to one another is called the equator of the capsular bag. Each of the two membranes has in each case an inner interface with respect to the interior space of the capsular bag and an outer interface with respect to the interior space of the capsular bag. For clarity, these are abbreviated here to inner and outer interfaces of the anterior or posterior membrane.

For determination of the shape and/or position of the eye lens, the control unit preferably identifies one or both interfaces of the lens by irradiating said lens by means of the laser and analysing the backscattered radiation by means of the measuring equipment. From the drop in backscatter intensity between the anterior and the posterior interface, the interfaces and therefore the shape and/or position of the lens can be determined with a high accuracy. Alternatively or additionally, an image recognition algorithm can be used for the identification. It is also possible to have the interfaces determined manually by operating personnel. Furthermore, tissue structures within the lens can advantageously be identified. For example, the core region (nucleus) and/or edge region (cortex) can be detected.

The interfaces are identified, for example, by determining an increase in intensity of the detection light between a first focal depth and a second focal depth and a decrease in the intensity of the detection light between a third focal depth and a fourth focal depth. The anterior and posterior interfaces are distinguished in that the backscatter is significantly higher when focussing a scanning point in the interface than when focussing scanning points outside or inside the lens. The interfaces therefore can be identified with a low outlay by determining an increase and decrease in the intensity of the detection light. The interfaces of the capsular bag membranes can also be identified in this manner. Even if under certain circumstances the two interfaces of one of the capsular bag membranes cannot be resolved visually, measurement of one of the two interfaces of the capsular bag membrane in question or of the adjacent interface of the lens is sufficient, since the capsular bag membranes have a known thickness of from 5 µm to 20 µm and run at least approximately parallel to one another and to the lens interface.

In addition to or instead of automatic irradiation of the capsular bag by known methods for prophylaxis of PCO or treatment of PCO, automatic measurement of the characteristic interface(s) also makes possible automatic irradiation for prophylaxis of PCO or treatment of PCO in accordance with several novel aspects:

According to a first aspect of the invention, in one method for the prophylaxis of posterior capsule opacity by means of a short pulse laser or an ultra-short pulse laser, a target volume is irradiated by at least one laser pulse such that at least one (preferably acoustic) pressure wave emanates from the target volume and hits at least one membrane of the capsular bag of an eye without tearing said membrane. Preferably, the target volume is chosen such that the pressure wave reaches at least the anterior membrane. In this context, a pressure wave is to be understood as meaning pressure variations of any type in the ocular tissue which spread out in the form of waves. The pressure wave generated by an fs laser, for example, is extremely weak and has an extremely low range, which precisely represents the advantage of the laser (protection of the surroundings). In the case of an fs laser, a target volume which lies correspondingly close to the membrane is therefore to be irradiated, for example a target volume, the centre of which is a target volume radius away from the interface. Preferably, the target volume determined lies completely within an interior space of the capsular bag, as a result of which impairment of the membrane(s) is minimal.

The energy of the laser pulse can be predetermined The position of the target volume, that is to say its coordinates, is then determined, for example with respect to the distance from the membrane, such that in spite of the impingement of the pressure wave the membrane remains free from tears (as long as it was free from tears beforehand). The energy of the laser pulse can optionally also be determined with this aim. The determination of the coordinates (and in the second case of the energy) is effected, for example, by a simulation calculation or by means of a look-up table. The target volume can also be irradiated with several laser pulses.

As a result of the pressure wave or, in the case of an ultra-short pulse laser, as a result of the energy introduced into the target volume close to the membrane, LECs and biological deposits responsible for a later LEC proliferation which have settled on the inside of the membrane are destroyed, detached or at least impaired in their growth (deactivated). The development of PCO can thus be prevented or at least significantly reduced. It is also possible to eliminate or at least to reduce existing PCO.

The position of the target volume (and optionally the pulse energy) is expediently determined such that the pressure wave hits the anterior and/or the posterior capsular bag membrane, in particular hits the capsular bag membrane(s) in question in the area of an equator of the capsular bag. As a result, the LECs are destroyed, detached or at least impaired in growth with a high efficiency. In this manner, PCO can be prevented, reduced or eliminated with corresponding efficiency.

According to the first aspect of the invention, an ophthalmologic laser device of the type mentioned at the outset has a control unit which is configured to implement the following steps:
determination of the shape and position of at least one (preferably the inner) interface of a (preferably the anterior) membrane of a capsular bag of an eye located in the treatment area by means of the measuring equipment,
determination of the coordinates of a target volume such that, on irradiation of the target volume with a laser pulse of predetermined pulse energy, a (preferably acoustic) pressure wave runs from the target volume at least up to the anterior and/or posterior membrane without tearing said membrane,
adjustment of the deflector unit to the target volume determined (such that the beam runs through the coordinates thereof) and irradiation of the target volume with at least one laser pulse of the predetermined pulse energy by means of the laser.

The target volume can also be irradiated with several laser pulses. Preferably, the control unit determines the coordinates of the target volume such that it lies completely in the capsular bag, i.e. between the anterior and the posterior capsular bag membrane.

With a laser device of this type, automatic measurement of the characteristic interface(s) can be used for automatic destruction, detachment or at least impairment in growth of LECs by irradiation of the interior space of the capsular bag for the purpose of prophylaxis of PCO or treatment of PCO. Compared with the prior art the outlay, in particular the time outlay, for prophylaxis or treatment is reduced and the probability of the (re)occurrence of PCO is reduced. The pressure wave generated by an fs laser is extremely weak and has an extremely low range, which precisely represents an advantage of the laser (protection of the surroundings). In the case of an fs laser, it is therefore an equivalent alternative to determine the target volume such that its centre lies a target volume radius away from the anterior (or posterior) membrane.

The interfaces of the anterior and the posterior membrane can expediently be measured with respect to their shape and position. If the resolution of the measuring equipment is better than the thickness of the capsular bag membranes, the inner and outer interfaces of the anterior and the posterior membrane can be measured separately with respect to their shape and position and used for determination of the target volume coordinates.

In this context, the laser device is expediently configured (in particular focussed) such that the laser pulse has a duration and/or an energy such that in tissue located in the target volume
photodisruption occurs and triggers the pressure wave, or
a photodisruption-free, non-linear interaction (below an energy threshold above which the photodisruption would start) occurs which detaches cells or molecules from a membrane or deactivates them. In this context, the focussing, i.e. the size of the target volumes, can be predetermined or determined and adjusted by the control unit.

Preferably, the control unit can be configured to determine the coordinates of the target volume relative to the inner interface of the anterior membrane, in particular as a function of a prognosticated diameter of the target volume, and in particular at a predetermined distance from this interface. Whether a pressure wave tears the membrane depends on its intensity, which in its turn depends on the energy introduced and decreases with increasing distance from the target volume. Due to the relative positioning of the target volumes with respect to the inner interface, a destruction-free impingement of pressure waves on the anterior capsular bag membrane can be made possible with a low outlay.

Embodiments are advantageous in which the control unit is configured for determination of the coordinates of several different target volumes and for successive adjustment of the deflector unit to said target volumes and irradiation of said target volumes. PCO can be suppressed or treated with a high efficiency by multiple irradiation.

The pulsed laser is expediently an ultra-short pulse laser for emission of femtosecond pulses or picosecond pulses or a short pulse pulsed laser for emission of nanosecond pulses. With these types of laser, both photodisruptions and non-linear interactions below the disruption threshold can be generated with a low outlay.

According to a second aspect of the invention, in a method for prophylaxis of posterior capsule opacity by means of an ultra-short pulse laser several target volumes, which each lie at least partially in an anterior membrane of a capsular bag of an eye, are irradiated by in each case at least one laser pulse such that a region of the anterior membrane which lies away from a visual axis penetration zone of this membrane (that is to say does not include this and therefore lies outside the opening area of an anterior capsulotomy/capsulorhexis) is partially or completely perforated along its periphery. The irradiated target volumes thus lie either completely or partially in the anterior capsular bag membrane. One or more of the target volumes can also be irradiated with several laser pulses. The visual axis penetration zone is that area of the anterior membrane through which the visual axis of the eye runs. The region is expediently perforated all around. Several different regions can advantageously be perforated in this manner (in each case partially or in each case completely). Preferably, the determination of the target volumes for each region is carried out such it lies outside the lens area of the IOL to be implanted, i.e. in the area of the haptics of the IOL. The mechanical stability of the remaining inner capsular bag area which covers the edge of the lens is thereby retained. The haptics area is that diameter area of the capsular bag in which the haptics of the IOL are (usually) located.

The tissue separated in this manner is expediently removed later, for example by suction of the lens fragments. On removal of the tissue, one hole per perforated region is opened in the anterior membrane, through which the aqueous humour can flow. The probability of the development of PCO can thereby be reduced significantly. Contact with aqueous humour presumably prevents the growth of LECs or at least significantly reduces it. If several flow holes are opened in the anterior membrane, the aqueous humour can circulate better through the capsular bag. The probability of the development of PCO can thereby be reduced further. Since the regions lie away from the visual axis penetration zone, the eyesight is not impaired. However, it is expedient to perforate the regions in the same work step in which a capsulorhexis incision (more precisely: capsulotomy incision) is made in the anterior membrane by ultra-short pulse laser.

According to the second aspect of the invention, an ophthalmologic laser device of the type mentioned at the outset having an ultra-short pulse laser has a control unit which is configured to implement the following steps:

determination of the shape and position of at least one interface of an anterior membrane of a capsular bag of an eye located in the treatment area by means of the measuring equipment, determination of the coordinates of several target volumes such that these each lie at least partially in the anterior membrane and, on irradiation of the target volumes with in each case at least one laser pulse of predetermined pulse energy, a border of a region of the anterior capsular bag membrane is perforated photodisruptively, this region lying away from a visual axis penetration zone of the anterior capsular bag membrane, in particular in the area of the haptics of an IOL to be implanted, for each of the target volumes: adjustment of the deflector unit to the target volume (such that the beam runs through the coordinates thereof) and irradiation of the target volume with at least one laser pulse of the predetermined pulse energy by means of the pulsed laser.

With a laser device of this type, automatic measurement of the characteristic interface(s) can be used for automatic cutting of a flow hole by irradiation of the anterior membrane of the capsular bag for the purpose of prophylaxis of PCO. Compared with the prior art the outlay, in particular the time outlay, for the prophylaxis and the probability of the occurrence of PCO are reduced.

If the resolution of the measuring equipment is better than the thickness of the capsular bag membranes, the inner and outer interfaces of the anterior and the posterior membrane can be measured separately with respect to their shape and position and used for determination of the target volume coordinates.

The control unit can expediently be configured for determination of the coordinates of several different target volumes and for successive adjustment of the deflector unit to said target volumes and irradiation of said target volumes such that these each lie at least partially in the anterior membrane and, on irradiation of the target volumes with in each case at least one laser pulse of predetermined pulse energy, edges of several regions of the anterior capsular bag membrane are perforated photodisruptively, these regions lying away from a visual axis penetration point of the anterior capsular bag membrane. By means of several flow holes, the probability of the occurrence of PCO is reduced still further.

According to a third aspect of the invention, in a method for prophylaxis of posterior capsule opacity by means of an ultra-short pulse laser several target volumes, which each lie at least partially in a posterior membrane of a capsular bag of an eye, are irradiated by in each case at least one laser pulse such that a region of the posterior membrane which lies around a visual axis penetration zone of this membrane is partially or completely perforated along its periphery. The irradiated target volumes thus lie either completely or partially in the posterior capsular bag membrane. One or more of the target volumes can also be irradiated with several laser pulses. The perforated region can be, in particular, a flap which is still connected to the posterior membrane at one point. Alternatively, the region can be perforated all around. Preferably, the posterior capsulotomy incision is made in the context of a cataract operation using an ultra-short pulse laser directly after the IOL implantation.

The perforation of a central region of the posterior capsular bag membrane by means of an ultra-short pulse laser makes possible a highly accurate posterior capsulotomy as prophylaxis of PCO or treatment of PCO. Due to the low energy of the laser pulses and the positioning in the posterior membrane, the risk of side effects is reduced significantly.

According to the third aspect of the invention, an ophthalmologic laser device of the type mentioned at the outset having an ultra-short pulse laser has a control unit which is configured to implement the following steps:

determination of the shape and position of at least one interface of a posterior membrane of a capsular bag of an eye located in the treatment area by means of the measuring equipment, determination of the coordinates of several target volumes such that these each lie at least partially in the posterior membrane and, on irradiation of the target volumes with in each case at least one laser pulse of predetermined pulse energy, a border of a region of the posterior capsular bag membrane is perforated photodisruptively, this region lying around a visual axis penetration zone of the posterior capsular bag membrane (that is to say including the visual axis penetration zone), for each of the target volumes: adjustment of the deflector unit to the target volume (such that the beam runs through the coordinates thereof) and irradiation of the target volume with at least one laser pulse by means of the pulsed laser of the predetermined pulse energy.

With a laser device of this type, automatic measurement of the characteristic interface(s) can be used for automatic posterior capsulotomy by irradiation of the posterior membrane of the capsular bag for the purpose of prophylaxis of PCO or treatment of PCO. Compared with the prior art the outlay, in particular the time outlay, for the prophylaxis or treatment is reduced.

If the resolution of the measuring equipment is better than the thickness of the capsular bag membranes, the inner and outer interfaces of the anterior and the posterior membrane can be measured separately with respect to their shape and position and used for determination of the target volume coordinates.

One embodiment which is particularly advantageous comprises a short pulse laser in addition to the ultra-short pulse laser, wherein the control unit is additionally configured for determination of the coordinates of a target volume in the area of the perforated region such that, on irradiation of this target volume with at least one laser pulse of predetermined short pulse energy, tissue is dislodged from the perforated region with the short pulse laser. If the tissue area perforated in the posterior capsulotomy is not or not completely detached from the posterior membrane, complete detachment can be achieved in this manner.

In all three aspects of the invention mentioned above, the laser device can advantageously be modified according to the embodiments described in the following:

In particular, the control unit can be configured to determine the coordinates of the target volumes with the aid of the shape and position determined for at least one of the interfaces, in particular to determine them relative to the interface of the membrane (3.6A/B), in particular to determine them as a function of a prognosticated diameter of the target volume (V) and in particular to determine them at a predetermined distance from the interface. The relative positioning of the target volumes with respect to the inner interface makes possible irradiation for treatment of PCO or prophylaxis of PCO with a high accuracy.

One embodiment of the laser device having a fixing device for detachable fixing of a position of the eye relative to the focussing lens system is particularly advantageous, the control unit being configured to fix the eye by means of the fixing device before the first determination of the shape and position of the interface(s) and to release the fixing only after the last irradiation of a target volume. This makes it possible for the eye still to occupy the same position relative to the focussing lens system during the irradiation as during the measurement of the characteristic interface(s).

In an embodiment of this type, it is expedient for the control unit to be configured to carry out, after the fixing and before the release of the fixing, at least one of the following additional incisions by means of the laser or an additional laser:

lens fragmentation incisions (for phacoemulsification),
corneal access incisions (for passing through a suction device for sucking off lens fragments after the phacoemulsification and an IOL, optionally also a phacoemulsification probe for fragmentation of the lens by means of ultrasound or laser radiation),
capsulorhexis incisions in an anterior capsular bag membrane (for passing through a suction device for sucking off lens fragments after the phacoemulsification and an IOL, optionally also a phacoemulsification probe for fragmentation of the lens by means of ultrasound or laser radiation),
limbal relaxing incisions.

Several work steps of a cataract operation can be performed in one session in this manner, which reduces the outlay, in particular the time outlay. The prophylaxis of PCO can in this way be integrated into a cataract operation in a manner which is advantageous for the patient and for the practitioner.

Advantageously, the fixing of the eye can be released only after a phacoemulsification has been carried out, including removal by suction of lens fragments and introduction of an IOL. By this means, all the work steps of a cataract operation can be carried out during a single session. This considerably reduces the outlay, in particular the time outlay. In particular, the reduced duration of an operation leads to an increased acceptance of the treatment by patients.

The treatment beam path preferably runs as a free beam through the cornea and pupil of the eye. By this means, the introduction into the eye of a local laser source for the incision of the anterior (optionally posterior) capsulorhexis and for phacoemulsification can be dispensed with. By this means, the mechanical stress on the eye is reduced considerably, which reduces the probability of complications.

The detection beam path is expediently coupled out of the treatment beam path, in particular by means of a beam splitter. By this means, the treatment beam path can be used for detection. The coinciding of the coordinate systems of measurement and irradiation makes possible irradiation with a high accuracy and therefore minimises the probability of complications or side effects.

One advantageous embodiment comprises an ultra-short pulse laser and a short pulse laser, wherein the beams of these two lasers run partially coaxially in the treatment beam path. It allows irradiation with laser pulses of very different energy, in particular the combination of various aspects of the invention. The ultra-short pulse laser allows highly accurate incisions (perforations) with minimal effects on the surroundings of the target volume, for example capsulotomy incisions and corneal incisions. The short pulse laser allows rapid incisions, if greater effects on the surroundings of a target volume are acceptable, and the generation of pressure waves. As a result of the two lasers running partially coaxially, both operate in the same coordinate system, which makes possible a sequential irradiation of the same target volume or adjacent target volumes with the two lasers with a high accuracy.

Preferred measuring equipment comprises an optical coherence tomograph, a Scheimpflug camera or a detector for confocal reception of light from the target volume along a detection beam path. This allows measurement of the characteristic interface(s) with a high accuracy.

It also lies within the context of the invention to use several measurement methods and in particular different measuring equipment for measurement of the interface(s). It is thus advantageous in particular to combine confocal detection with optical coherence tomography (that is to say a confocal detector with an optical coherence tomograph/OCT). In this context, confocal detection with the attenuated therapy beam is accurate in position, which is not the case with an OCT module (measuring equipment) with a different beam source. A quasi-real time (online) swept-source OCT method (ss) can thus be calibrated by balancing the OCT measurement results with navigation data of the confocal detection. In addition or alternatively, OCT measurement parameters, such as the start coordinates, can be determined with the aid of confocally detected navigation data (recording of the OCT measurement in the confocal navigation data). In this context, for example at places where a particularly high positioning accuracy is required, confocal detection is first carried out and optical coherence tomography is then applied over a large area, starting from the points determined for the interfaces.

In order to be able to measure interfaces accurately by means of the OCT method, a short coherence length of the beam source of the OCT measuring equipment is expedient. Preferably, the coherence length of the beam source of the OCT measuring equipment is therefore less than 12 µm. On the other hand, the time for measurement of an interface increases sharply with increasing image resolution. The coherence length is therefore preferably chosen in the range of from 4 µm to 12 µm. The range of from 4 µm to 6 µm is particularly preferably chosen in this context. An optimum ratio of spatial resolution and duration of the measurement of the surface results for this range.

It is particularly advantageous if confocal detection of an interface or another position to be measured is carried out in a first step. In a second step, the energy which leads to the change in the property of the irradiated material is introduced at this position using the pulsed laser, in particular the ultra-short pulse laser. This change can be, in particular, a perforation of the capsular bag. In a further step, this perforated position can be visualised by means of OCT and can thus be used to control the positioning of an ultra-short pulse laser or another laser. The other laser can be, for example, a short pulse laser. The interplay of confocal detection and OCT navigation thus ensures a calibration of the OCT navigation of pinpoint accuracy for the individual patient and provides the prerequisite for highly accurate positioning of the laser shots in the target space.

A similar accuracy can be achieved by first carrying out a global measurement of interfaces (for example all the ocular interfaces) by OCT and then measuring the characteristic interface(s) (for the action to be performed) by means of confocal detection only at individual base points. By this means, the slower confocal detection needs to be carried out only in a part volume of the eye.

The following embodiments are advantageous for all three aspects of the invention mentioned above:

Embodiments in which the irradiation is carried out while a natural eye lens is (still) located in the interior space are particularly advantageous. By this means, on the one hand, the later suction procedure for lens fragments can also be used to remove tissue separated off from flow hole regions or anterior or posterior capsulotomy regions. On the other hand, irradiation of an IOL, which under certain circumstances could lead to an impairment of the transparency or the life of the IOL, can be omitted in this way. In the first aspect of the invention, the irradiation can be carried out for elimination/suppression of the LECs before or after phacoemulsification of the natural lens, but advantageously before the removal by suction of lens fragments, preferably even before the incision of an anterior capsulorhexis. In the second aspect of the invention, the irradiation can be carried out before or after phacoemulsification and IOL implantation. In the third aspect of the invention, the irradiation should be carried out only after phacoemulsification and IOL implantation, in order to avoid the risk of a vitreous body prolapse.

Embodiments in which the irradiation is carried out while an artificial eye lens is located in the interior space are also advantageous. This applies in particular to embodiments with ultra-short pulse lasers, since these have significantly weaker effects on the IOL due to the lower energies. Alternatively, the irradiation can be carried out while no eye lens is located in the interior space. By this means also, irradiation of the IOL is avoided.

In all the methods according to the invention, a shape and a position of at least one interface of a membrane of the capsular bag is preferably determined before the irradiation, and a site, that is to say the coordinates, of the target volume is determined with the aid of the shape and the position of the interface. The determination of the coordinates with the aid of the measurement values of the characteristic interface(s) makes possible—as already stated above—irradiation with a high accuracy and a low outlay, in particular time outlay.

In all the above-mentioned embodiments, the control unit can have in each case a software module for carrying out a method step. It is possible for one software module to be configured for carrying out several or even all of the method steps.

Preferably, the control unit is constructed such that a laser application pattern for prophylaxis of aftercataract formation is integrated therein and is used for determination of the coordinates of target volumes. For example, for determination of the coordinates of the target volumes, the control unit can record an image of the eye by means of a camera and determine anatomical structures therein by means of image recognition. With the aid of the structures determined, in particular the shot patterns (chronological sequence of the target volumes) and the target volumes can be matched to geometries recognised by the algorithm.

In all the embodiments the laser focus beamed into the target volume can be not only spherical or elliptical, but also linear or circular, in order to optimise the treatment efficiency or the spatial propagation of pressure.

For a fixing device of the type mentioned at the outset for coupling an eye of a patient to an ophthalmologic laser device, it is envisaged that the suction device is interrupted at least at one point, preferably at two points. A fixing device of this type makes possible removal by suction of lens fragments and introduction of an IOL in the fixed (docked) state of the eye through the interruption(s) and therefore a highly accurate cataract operation in a single laser session. Compared with the prior art, this means a reduced outlay, in particular time outlay, a reduced probability of side effects and complications and a greater acceptance by the patient. Preferably, the at least one interruption is constructed for passing through an irrigation/aspiration device for lens fragments which is known per se, in particular with construction of the interruption for passing through a phacoemulsification probe which is known per se. A width of the interruption of from 2 mm to 5 mm is particularly preferred.

In one advantageous embodiment, the disc can have on its edge at least one recess corresponding to the interruption (in the case of two interruptions preferably two recesses) for passing through the irrigation/aspiration device. By this means, surgical operating instruments known per se, such as the irrigation/aspiration device, can be passed through the cornea at a particularly steep angle, which reduces mechanical stress on the cornea.

In particular, the disc can be mounted such that it can move relative to the suction device, in order first to produce laser incisions through the disc, in particular incisions in the cornea as access for passing through surgical instruments, such as the irrigation/aspiration device. A fixing device of this type can be switched between two states. In the first state, the disc is disposed such that a target volume, which lies alongside the interruption of the suction device, can be irradiated through the disc, while the recess lies away from the interruption (and away from the target volume). In this state, incisions serving as access for surgical instruments can be cut into the cornea by means of the laser through the disc. In the second state, the recess is adjacent to the interruption of the suction device (and lies in front of the target volume when viewed from the laser), so that a convenient grip on the access cut results.

The suction device can protrude from the disc on a side of the disc facing the eye, in particular to the extent that an irrigation/aspiration device can be passed through the interruption to an incision lying in the region of the disc. By this means, surgical instruments, in particular an irrigation/aspiration device, can be inserted into the eye through one or more accesses in the cornea which lie behind the disc (for example because they have been produced through the disc with a laser device).

In such an embodiment, an opening (for example known from infusion devices), in particular for passing through an irrigation/aspiration device for lens fragments, in particular for passing through a phacoemulsification probe, can be disposed in the interruption such that the suction device and the opening together close off from the surroundings of the fixing device, in a liquid-tight manner, a space enclosed by the projection with the disc and the eye. By this means, the space between the disc and eye can be filled with liquid, in particular with water, for the cataract operation. Surgical instruments, such as the irrigation/aspiration device, can then be inserted through the sealing opening, through the water and through the cornea into the eye.

A fixing device having a suction device which protrudes from the disc, but without a sealing opening in the interruption, can also be used to insert surgical instruments through an access in the cornea lying behind the disc, in that the space between the disc and eye remains filled with ambient air.

In all the embodiments of the fixing device it is possible to cut access incisions in the cornea mechanically, instead of perforating it by pulsed laser.

The invention is explained in more detail in the following with the aid of embodiments.

Figure 1B:
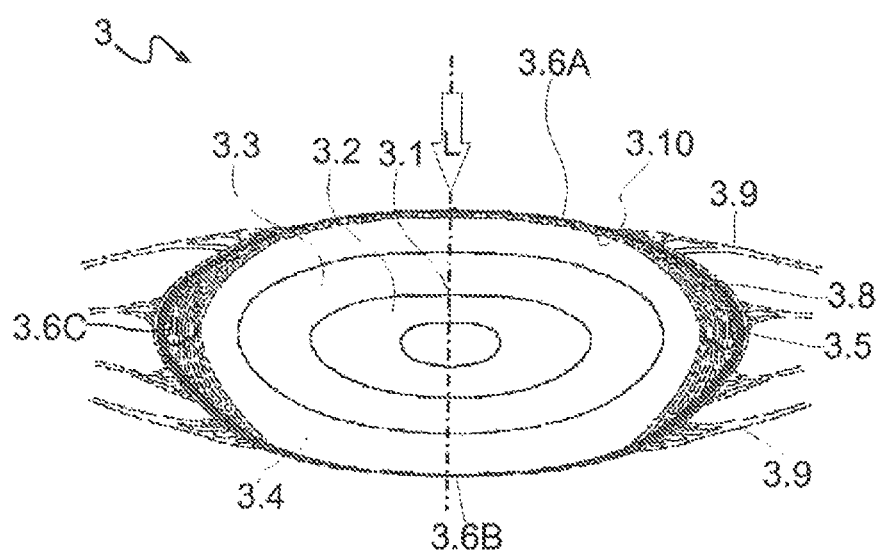

FIG. 1 shows a simplified diagram of the structure of the human eye 2 in the natural state. FIG. 1A shows the entire eye. FIG. 1B shows as an enlarged section therefrom of only the lens 3 and its immediate surroundings. Light can enter through the cornea 2.1 into the inside of the eye 2 and fall through the opening of the iris 2.2, the lens 3 and the vitreous body 2.3 onto the retina 2.4. The lens 3 comprises the embryonic nucleus 3.1, the foetal nucleus 3.2, the adult nucleus 3.3, the cortex 3.4 and the equatorial nucleus arc 3.5. It is held by a capsular bag, which comprises an anterior membrane 3.6A and a posterior membrane 3.6B and is connected to the zonular fibres 3.9 via a zonular lamella 3.8 in each case. The zonular fibres 3.9 hold the capsular bag in the eye at a defined position in order to make sharp imaging on the retina 2.4 permanently possible. Between the cortex 3.4 and the anterior membrane 3.6A, the LECs 3.10 are located on the inner interface of the anterior membrane 3.6A. After cataract surgery, they spread onto the inner interface of the posterior membrane 3.6B and thus lead to PCO.

A dot-dash line indicates the course of the visual axis through the lens 3. The zones on which the visual axis intersects the anterior membrane 3.6A and the posterior membrane 3.6B are referred to as the respective visual axis penetration zone.

Figure 2:
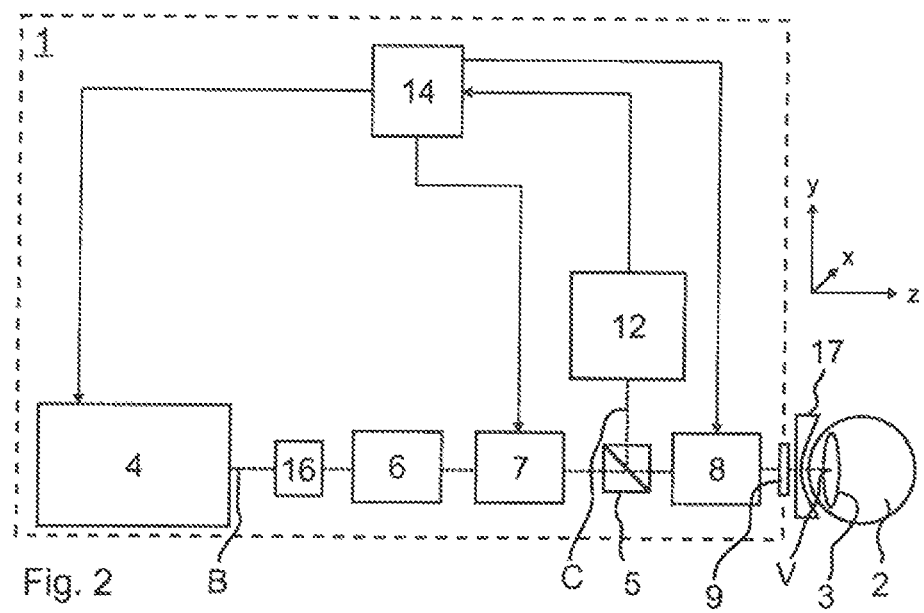
FIG. 2 shows an ophthalmologic laser device with OCT.

FIG. 2 shows a diagram of an example of an ophthalmologic laser device 1 which is envisaged for treatment and/or prophylaxis of PCO in an eye 2, in particular in the context of cataract surgery. It can be constructed for different aspects of the invention, in particular also for combinations thereof.

The laser device 1 has in the treatment beam path B a pulsed laser 4, for example a pulsed Ti:Sa infrared laser for emission of infrared radiation having a wavelength of 1064 nm and a pulse length of between 100 fs and 1,000 fs. The laser device 1 moreover has a beam splitter 5, a scanning lens system 6, an adjustable beam deflector unit 7, a focussing lens system 8 and a cover glass 9. Via the beam splitter 5, the detection beam path C of an optical coherence tomograph 12 is coupled out of the treatment beam path B. The OCT 12 is connected to a control unit 14. A modulator 16, for example an acousto-optic modulator (AOM, AOTF), is furthermore provided in the illumination beam path. A fixing device 17 for the eye 2, behind which lies the treatment area, is disposed between the laser system 1 and the eye 2.

The optical components, in particular the lens systems 6 and 8, are optimised, corrected and coordinated with one another with the aim of the best possible focus miniaturisation. For example, their optical aberrations are minimised to a high degree, so that only a low energy input is required for photodisruption. The optical components are configured such that the intrinsic dispersion of the intraocular media with respect to the change in pulse length and also the intrinsic focussing action of the gradient lens structure of the eye lens 3 are precompensated. By this means, the size of different target volumes can be kept constant with an error of at most 10% over the entire area of the eye lens 3 and over their entire depth.

The deflector unit 7 comprises, for example, a number of galvanometric mirrors for deflection of the laser radiation in the x and y direction over the eye lens 3. The focussing of the laser radiation in the z direction along the optical axis is achieved, for example, by a movable lens or lens group within the scanning lens system 6 or the focussing lens system 8 or by a movable tube lens (not shown). The pulsed IR laser radiation emerges from the laser 4 and is focussed via the scanning lens system 6, the scanner unit 7 and the focussing lens system 8 into a target volume V in the eye lens 3. By means of the deflector unit 7 and a movable lens or lens group within the scanning lens system 6 or the focussing lens system 8, the control unit 14 can shift the focus in the x, y and z direction so that another target volume V is irradiated.

The fixing device 17 in this context fulfils the tasks of coupling the patient's eye 2 mechanically to the optical construction of the apparatus 1, transmitting the optical radiations for navigation and therapy and—optionally—making possible mechanical access for probes or surgical instruments into the anterior chamber of the eye. The patient's eye 2 is expediently fixed before detection and/or therapy, for example is sucked on to the fixing device 17 by means of reduced pressure. In addition, the patient's head can be fixed (not shown). The patient's gaze can be kept as constant as possible by a suitable fixing aim (not shown). In this context, an adjustable compensation of the angle between the geometric and visual axis of the eye is possible.

Since a significantly increased backscatter occurs at interfaces, by means of the OCT measuring equipment 12 the control unit 14 can determine the position and shape of interfaces from the intensities detected with a low outlay. The control unit 14 can identify the various interfaces within each x-z plane or y-z plane, for example by simple serial numbering from the front (interface with the shortest distance from the focussing lens system 8 in the z direction) towards the back (interface with the longest distance from the focussing lens system 8 in the z direction). For example, at a z resolution of, for example, 1 μm the third interface from the front in the treatment area is the outer interface of the anterior capsular bag membrane 3.6A, the fourth is the inner interface of said membrane 3.6A, the eleventh is the inner interface of the posterior membrane 3.6B and the twelfth is the outer interface of said membrane 3.6B. With the aid of, for example, three or more points per interface, the control unit can fit, for example, a model of the eye lens with respect to a minimal deviation from the measurement values. The model then represents the shape and position of the interfaces measured.

For the interfaces, the model can include, for example, spherical surfaces, ellipsoids or conical sections, and the mathematical fit to the backscatter intensities measured can be carried out, for example, by shifting, tilting, cutting the boundaries, enlarging or extending in order to make possible a centring with respect to the actual position of the lens in the space and maintenance of safety zones. The model can reproduce, in particular, a tilting of the eye lens 3 towards the optical axis of the system 1.

Taking into account the shape and position of the characteristic interface(s), the control unit 14 then determines irradiation data, namely the coordinates of a target volume and a pulse energy, as a function of the irradiation target and irradiates the target volume as a function of the irradiation target with one or more laser pulses.

The model determined can be updated during the treatment, for example in order to take into account changes in the position of the ocular tissue due to any eye movements occurring during treatment. The irradiation control data which have not yet been transmitted into the ocular tissue are then expediently re-determined with the aid of the updated model.

The cornea 2.1 of the eye 2 can also be treated by laser surgery using this system. For treatment of the cornea of this type, the properties of the ocular tissue which can be identified are, for example, its anterior and/or its posterior interface for determination of thickness and as reference area(s), and an appropriate model can be fitted to these.

Figure 3A:
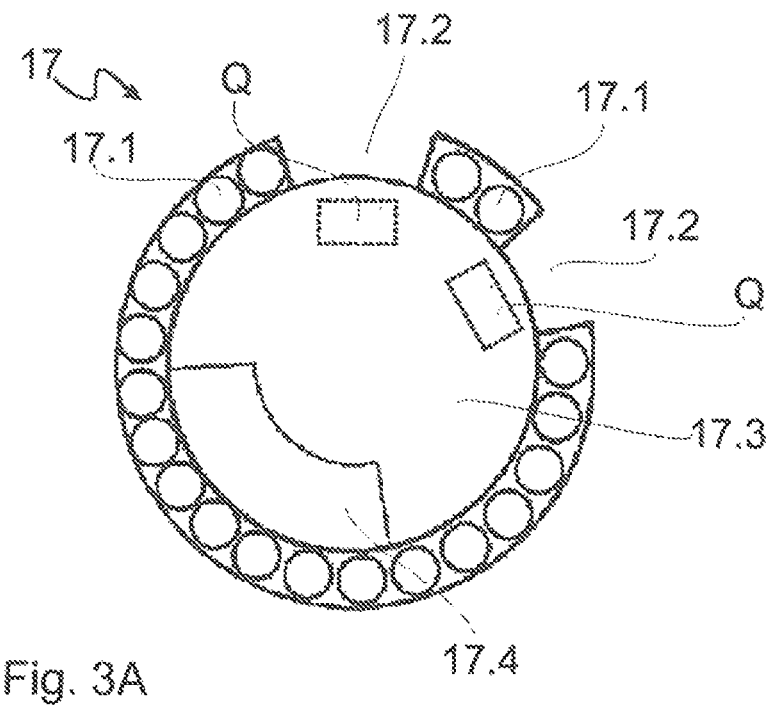
FIG. 3 shows a reversible fixing device.
Figure 3B:
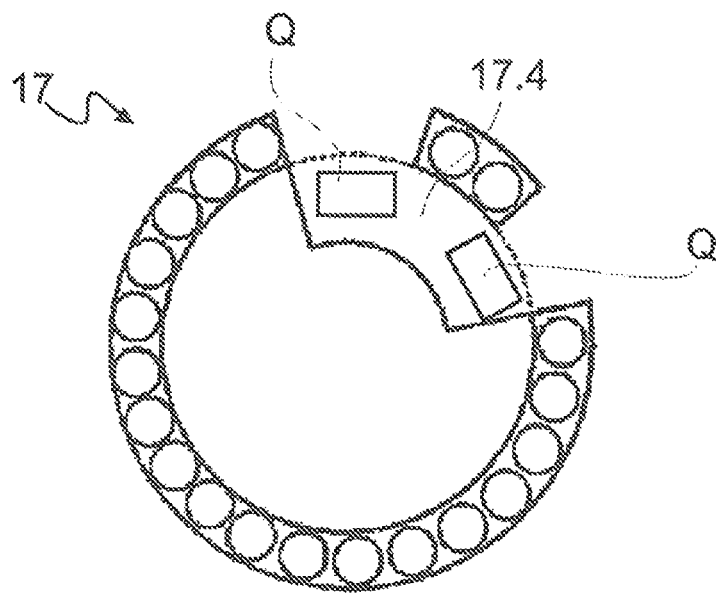

FIG. 3 shows a diagram of a fixing device 17 which can be switched into two different states and can be used, for example, in connection with a laser device 1 according to FIG. 2. FIG. 3A shows the first state which is envisaged for producing incisions Q in the cornea 2.1 by means of the laser 4. FIG. 3B shows the second state which is envisaged for insertion of probes or surgical instruments through the previously produced incisions Q.

The fixing device 17 comprises a suction ring, which is known in principle, as a suction device 17.1 which, however, is only partially constructed due to, for example, two interruptions 17.2 of a width of, for example, 5 mm each. It surrounds a disc 17.3, which is known in principle, but which has on the edge, for example, a recess 17.4 corresponding to the two interruptions 17.2. For switching between the two states, the disc 17.3 is movable, for example rotatable and/or axially movable, relative to the suction device 17.1. In the second state the incisions Q are accessible mechanically through the interruptions 17.2 and the recess 17.4.

The disc 17.3 can be, for example, flat on both sides in order to applanate the cornea 2.1 in the suctioned condition. Instead of the arrangement shown for the interruptions 17.2 and recesses 17.4, these can also be disposed, for example, diametrically opposed in each case. Embodiments with only one interruption 17.2 and only one recess 17.4, or with in each case three or more thereof, can also be realised.

Preferably, the holder for the (partial) suction ring 17.1 has mechanical guide devices for the surgical instruments. If liquid-tight openings, which are known per se (not shown), for probes and surgical instruments are disposed in the interruptions 17.2 and the suction device 17.1 protrudes from the disc 17.3 towards the eye, the intermediate space formed by the protrusion can be filled with water or a similar physiologically acceptable liquid. Alternatively, the intermediate space can be used as an air gap, and openings are then not required.

Ideally, the fixing device 17 is positioned on the eye 2 such that the boundary line between the suction device 17.1 and the disc 17.3 lies approximately along the limbus L.

Figure 4A:
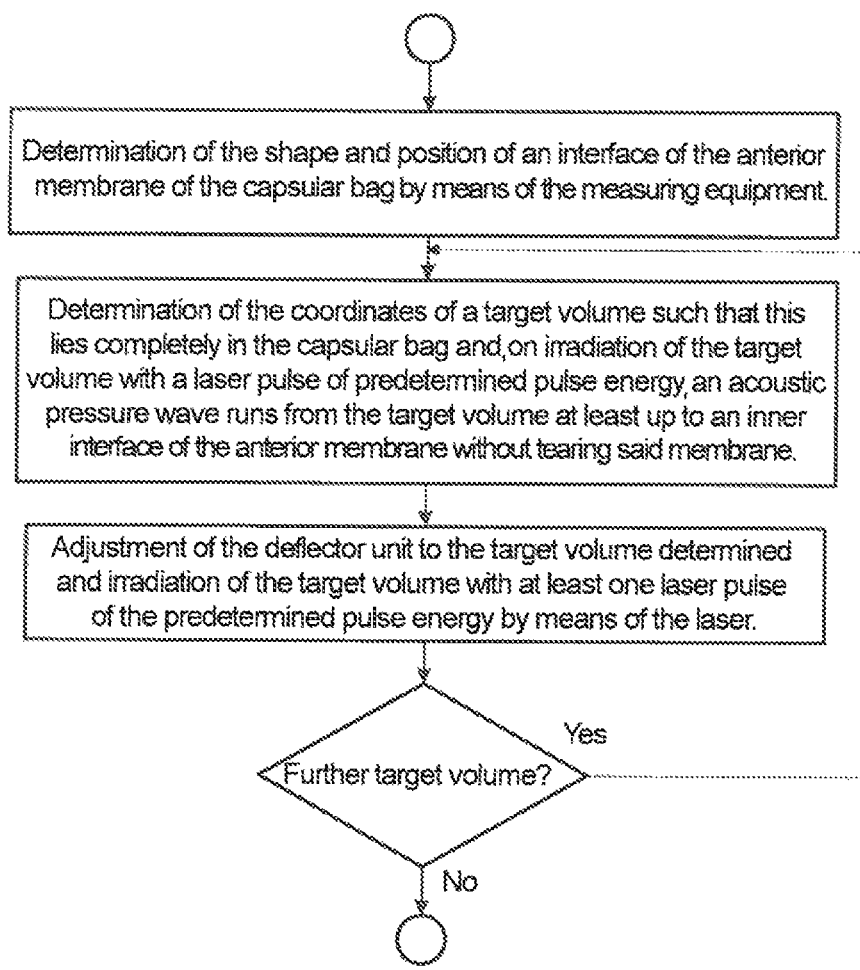
FIG. 4 is a flowchart of a method for prophylaxis or treatment of PCO according to the first aspect of the invention and a resulting target volume.

For prophylaxis or treatment of PCO, the control unit 14 carries out, for example, the operating method according to the first aspect of the invention shown in FIG. 4A. In this context, the same laser 4 is used for illumination during the detection phase (navigation phase) and irradiation during the treatment phase. In other embodiments (not shown) a different laser can be used for navigation than that used for treatment.

Using the model fitted, according to a specific treatment aim, here for example prophylaxis of PCO by LEC reduction, a quantity is determined of discrete target volumes V from which acoustic pressure waves run to the anterior capsular bag membrane 3.6A. For this purpose, the coordinates of the target volumes V are determined, for example, such that they are a constant distance from the inner interface of the anterior capsular bag membrane 3.6A. Irradiation control data are then determined from the coordinates of the target volumes V. The irradiation control data include, for example, control signals for the x and y-axes of the deflector unit 7 or for the internal z focussing and for the laser beam source and the output modulator 16 as well as for the pulse selector 18.

Directly after establishing the irradiation control data, the actual laser surgical intervention is performed at the treatment radiation output with the aid of the irradiation control data. In this context, for example, a photodisruption bubble (cavitation bubble) is produced in each target volume V by the laser radiation at a pulse frequency of 100 kHz to 1 MHz and a pulse length of less than 1 ps, in particular of 300 fs, with a pulse energy of preferably a maximum of 0.5 μJ. A pressure wave is emitted from each bubble. The constant distance of the inner interface of the anterior membrane 3.6A is predetermined such that at the predetermined pulse energy the pressure wave runs up to the anterior membrane 3.6A without tearing said membrane.

Due to the identical beam path for analysis and therapy, the system 1 is self-calibrating with respect to the observation position. Since the irradiation control data are determined with the aid of the information about the shape/structure/position of the lens determined with the identical beam path, therapy with a high accuracy is possible.

This method can also be performed with a short pulse laser as the laser 4. The constant distance is then correspondingly longer because of the higher pulse energy. For example, a pulse length of 0.5 ns to 10 ns at a pulse energy of 0.5 mJ to 10 mJ at a wavelength of 1064 nm is used to generate photodisruptions.

Figure 4B:
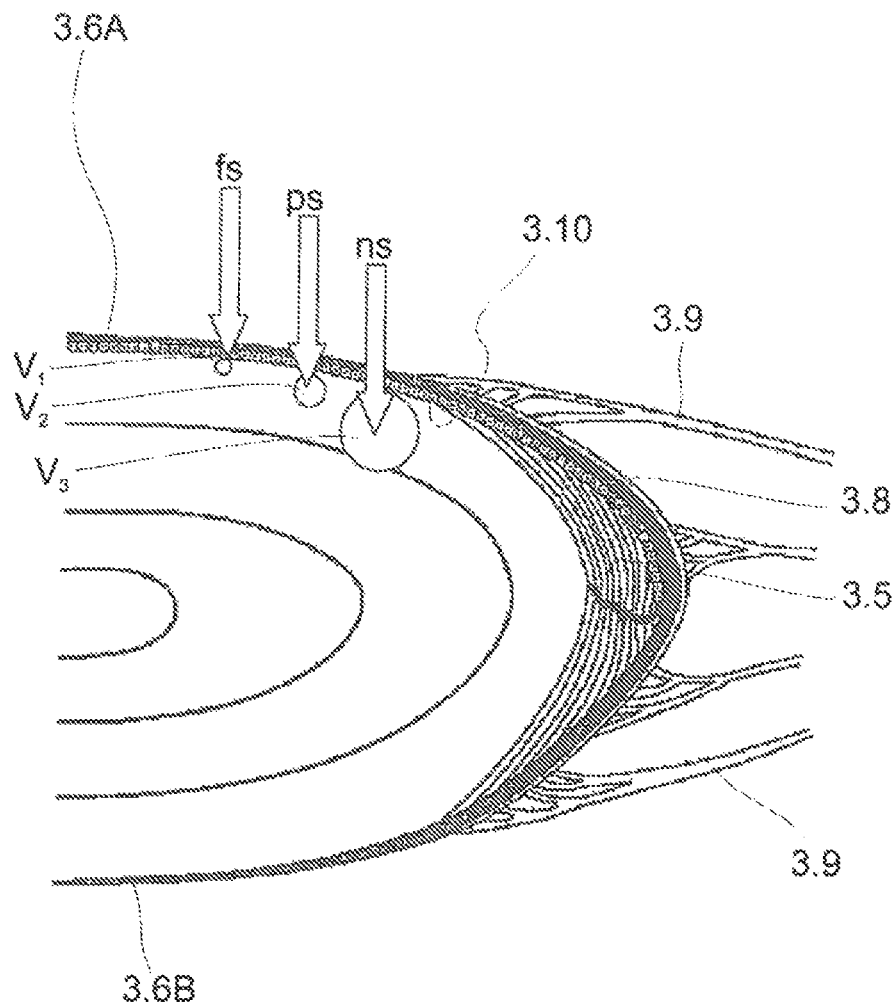

FIG. 4B shows a diagram of the generation of various cavitation bubbles with different lasers 4. An fs laser generates the smallest bubble, for example with a diameter of 10 μm, in the target volume $V_1$ with the lowest side effects. A ps laser generates a bubble of medium size, for example with a diameter of 60 μm, in the target volume $V_2$ with low side effects. An ns laser generates a large bubble, for example with a diameter of 300 µm, in the target volume $V_3$ with a correspondingly stronger pressure wave. The distance of the respective target volume $V_{1/2/3}$ from the membrane 3.6A/B in question must accordingly be greater for a greater target volume $V_{1/2/3}$ (that is to say larger bubble). In the case of fs pulses, the distance is preferably zero, and the centre of all the target volumes $V_1$ then lies in each case a radius of the particular target volume $V_1$, in the example shown that is to say 5 µm, away from the membrane 3.6A/B in question. In the case of ns pulses, the distance must be significantly greater than indicated in the drawing, in order to avoid tears in the membrane 3.6A/B.

Figure 5A:
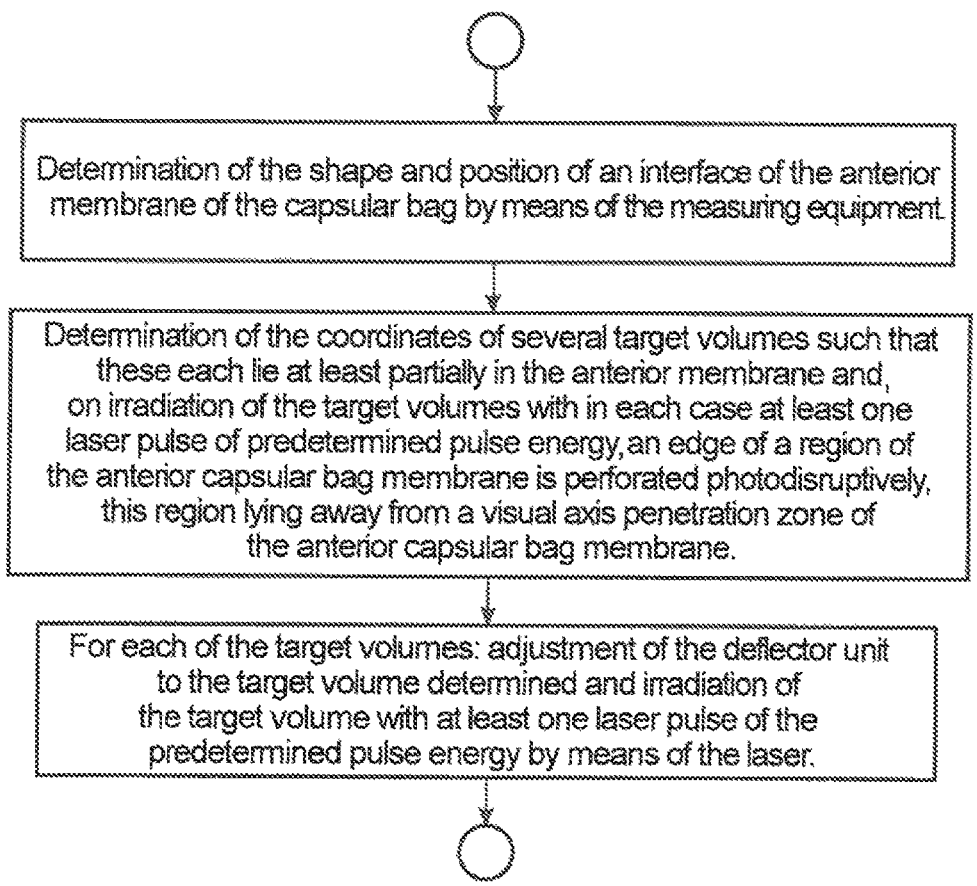
FIG. 5 is a flowchart of a method for prophylaxis of PCO according to the second aspect of the invention and resulting perforated regions.

For prophylaxis of PCO, the control unit 14 carries out, for example, the operating method according to the second aspect of the invention shown in FIG. 5A. The incision of the flow holes Z in the anterior membrane 3.6A requires an ultra-short pulse laser as the pulsed laser 4.

Figure 5B:
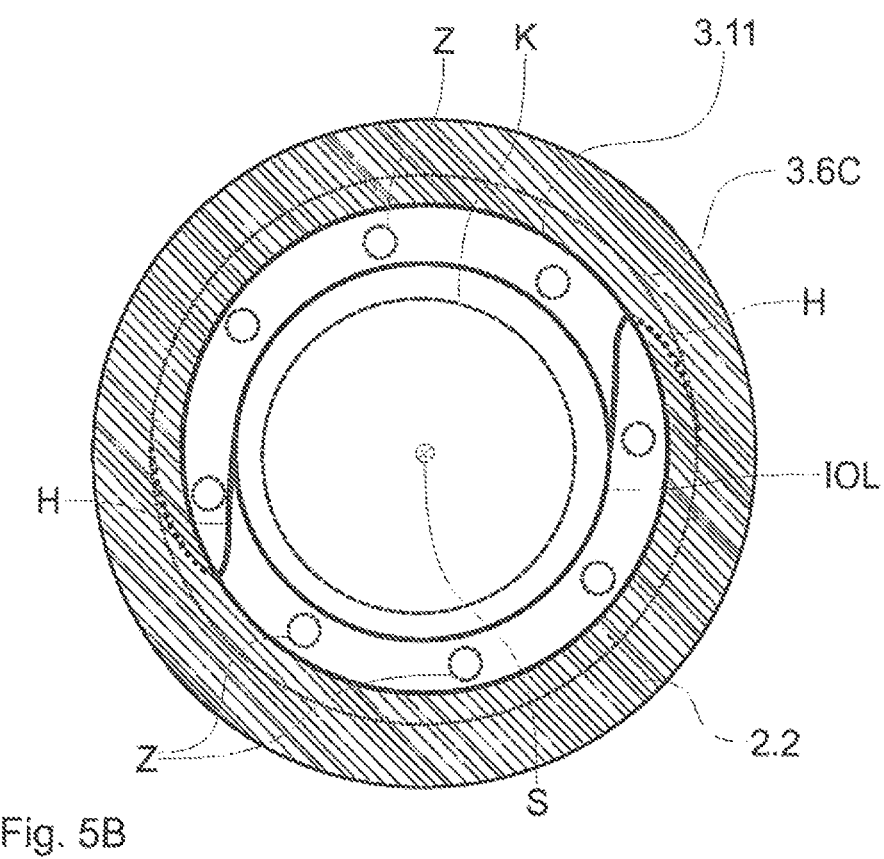

As a result, after removal of the perforated tissue, the flow holes Z shown in diagram form in FIG. 5B are present away from the visual axis penetration zone S. They lie on the edge of the area, accessible through the iris 2.2, of the anterior capsular bag membrane 3.6A in the area of the haptics H of the implanted IOL. The flow holes Z each have, for example, a diameter of from 0.25 mm to 0.75 mm.

The incision of the anterior capsulotomy opening K can also be made by means of the ultra-short pulse laser 4. It has, for example, a diameter of from 4 mm to 6 mm and includes the visual axis penetration zone S of the anterior membrane 3.6A. A posterior capsulotomy K can likewise be generated in this size range by means of the laser 4 (coincides in the parallel projection, for example, with the projection of the anterior capsulotomy K).

Figure 6:
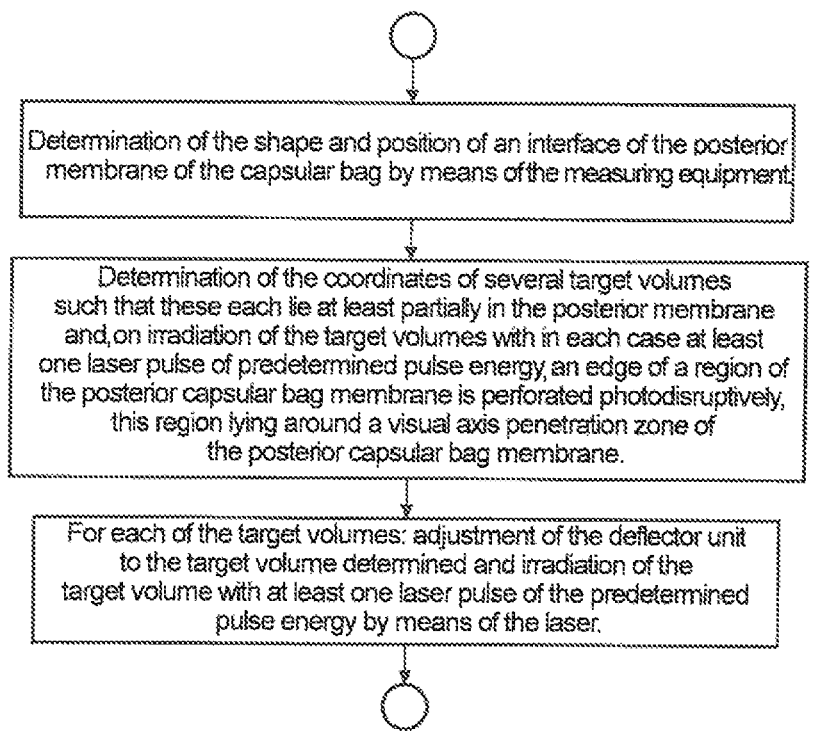
FIG. 6 is a flowchart of a method for prophylaxis or treatment of PCO according to the third aspect of the invention.

For prophylaxis or treatment of PCO, the control unit 14 carries out, for example, the operating method according to the third aspect of the invention shown in FIG. 6. The highly accurate incision, which is low in side effects, of a central capsulotomy in the posterior membrane 3.6B requires an ultra-short pulse laser as the pulsed laser 4. Compared with the conventional Nd:YAG short pulse laser, with an ultra-short pulse laser, in particular an fs laser or a ps laser, a gentler treatment results due to the lower disruption energies, which are reduced from several mJ to a few µJ. While in conventional Nd:YAG disruption lasers the focus is positioned behind the posterior capsular bag membrane 3.6B in order to destroy the membrane with the acoustic shock wave and to protect the artificial lens already inserted, with the aid of the highly repetitive ultra-short pulse laser and the coupled navigation the focussing is effected on or in the immediate vicinity of the membrane. A central part of the posterior capsular bag membrane 3.6B can be cut out precisely in this manner, without damaging surrounding tissue. If appropriate, after the perforation, local pressure waves can be generated in a defined manner by a few laser pulses of higher energy, in particular by an additional short pulse laser, if the membrane section cut out is held in its old position by adhesion and therefore is not immediately removed from the visual axis by itself. However, the pressure waves required in this case are so slight that only a dislocation but not a separating off of capsular bag tissue takes place. The irradiation is advantageously carried out directly after the IOL implantation.

An integration of one or more aspects of the invention into the procedure of a cataract operation is particularly advantageous. Preferably, all procedures of the cataract operation and the prophylaxis of PCO are then carried out with a laser device 1 such that the eye 2 is coupled to the laser device 1 only once, so that all the procedures are concluded within one session. A fixing device 17 as described for FIG. 3 is then preferably used for the coupling of the eye.

Figure 7:
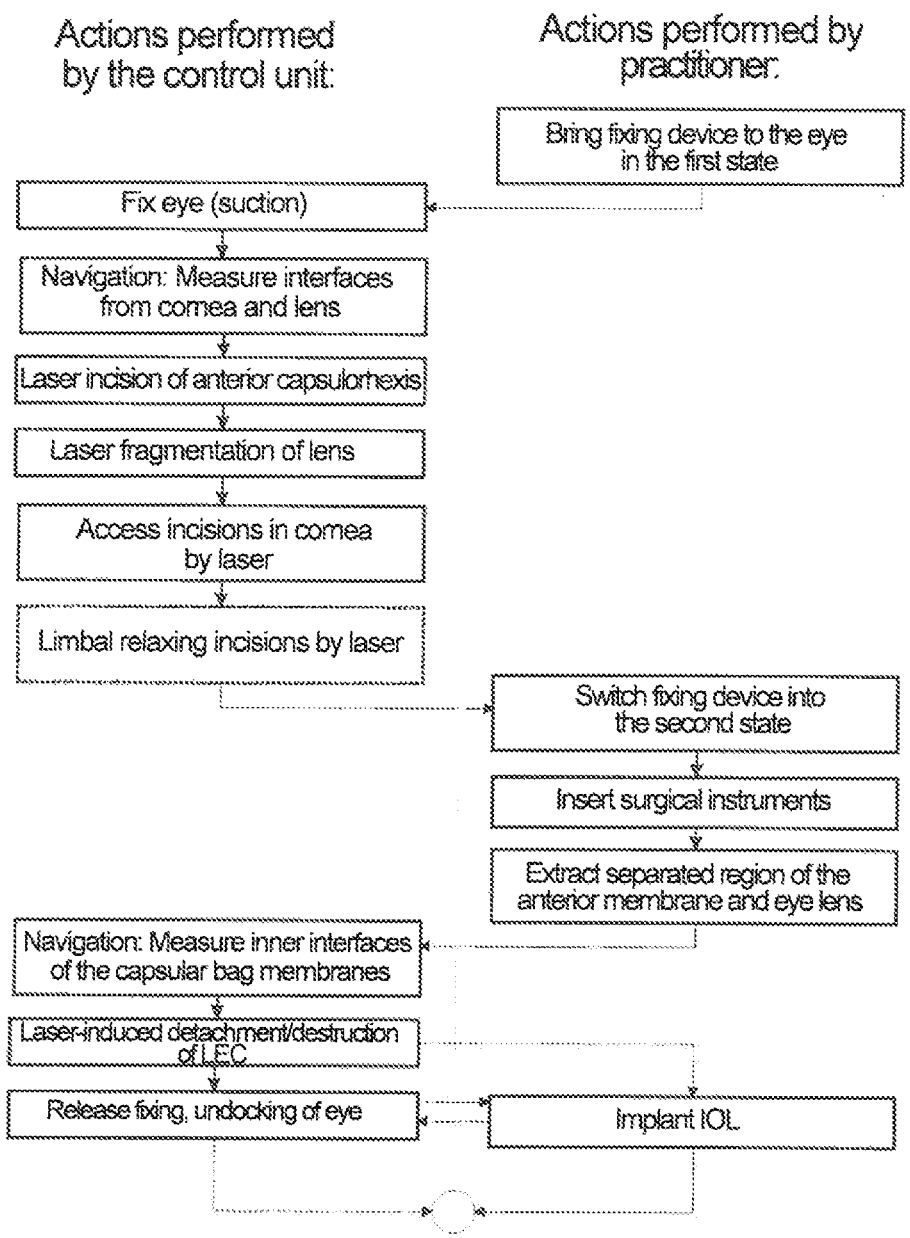
FIG. 7 is a flowchart of a complete cataract operation within one laser session, including the first aspect of the invention for prophylaxis of PCO.

FIG. 7 shows the procedure of an exemplary cataract operation with integrated LEC detachment as prophylaxis of PCO. The work step known per se with the broken outline is optional. The implantation of the IOL by the doctor can be carried out either before or after the uncoupling of the eye 2 from the fixing device 17.

Figure 8:
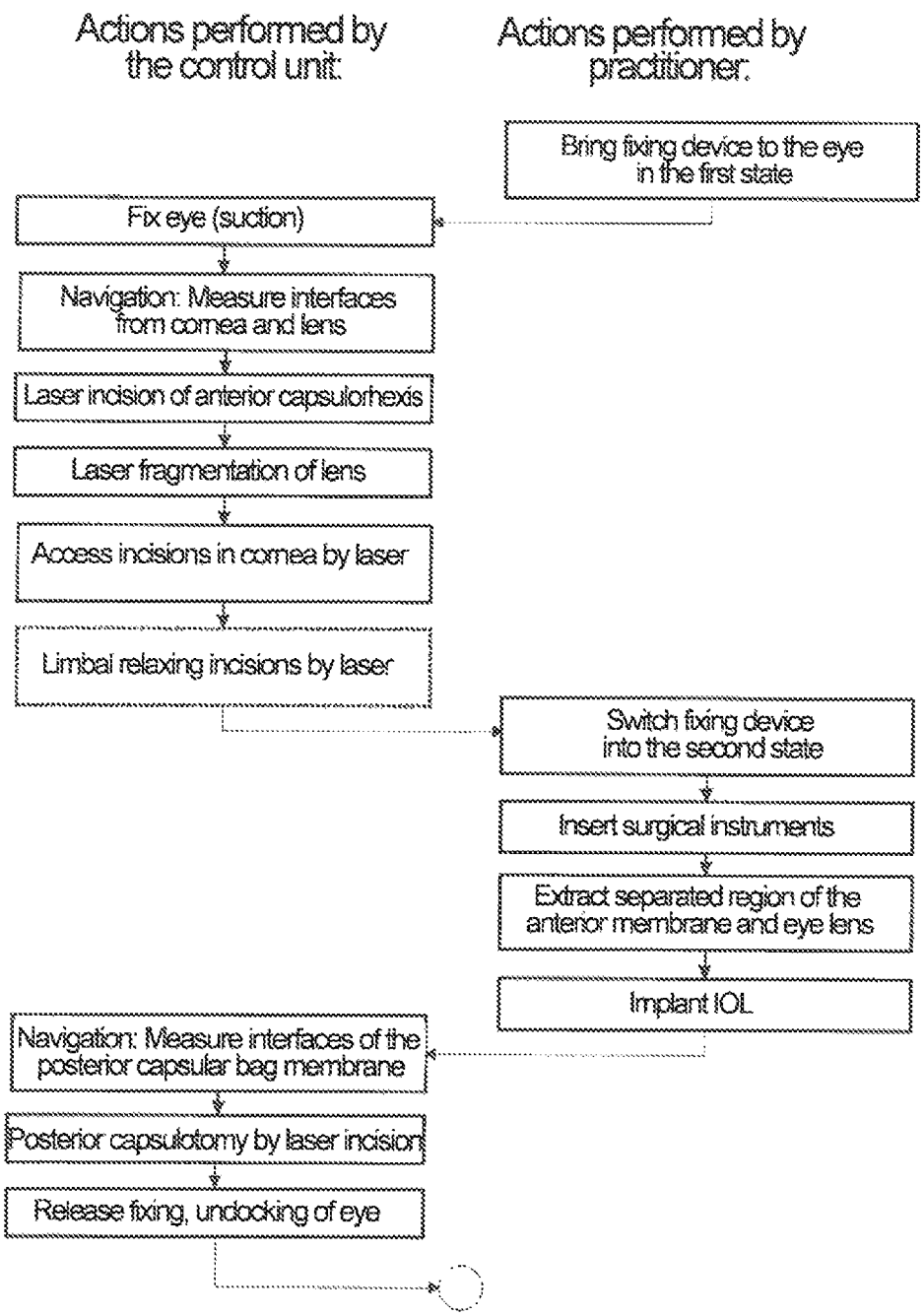
FIG. 8 is a flowchart of a complete cataract operation within one laser session, including the third aspect of the invention for prophylaxis of PCO.

FIG. 8 shows the procedure of an exemplary cataract operation with integrated LEC detachment as prophylaxis of PCO with integrated posterior capsulotomy as prophylaxis of PCO. The work step known per se with the broken outline is optional. The implantation of the IOL by the doctor is carried out here, for example, with a coupled eye 2 before the incision of the posterior capsulotomy by means of the ultra-short pulse laser.

Figure 9:
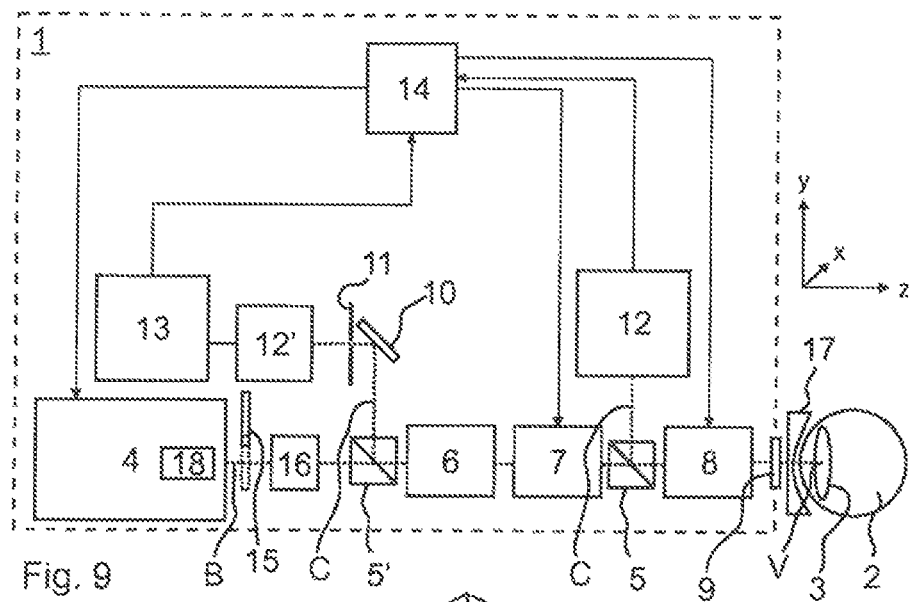
FIG. 9 shows an ophthalmologic laser device with OCT and confocal detection.

FIG. 9 shows an alternative laser device 1 which combines the OCT measuring equipment 12 with measuring equipment 11/12' for confocal detection. As in FIG. 1, the laser device 1 has a pulsed Ti:Sa infrared laser as the pulsed laser 4 in the treatment beam path B. The laser device 1 moreover has a polarisation beam splitter 5 and an optical phase delay system 9 as well as a deflection mirror 10, a confocal aperture 11 and a detector 12 with amplifier 12, which form a coupled-out detection beam path D. An attenuator 15 can be folded into the treatment beam path B. It serves to switch between an image-recording radiation output and a treatment radiation output. The image-recording radiation output is achieved with the attenuator 15 folded into the treatment beam path B, and the treatment radiation output is achieved without the attenuator 15. The optical phase delay system 9 is constructed, for example, as a 2λ-plate, which forms a cover for the laser system.

The detector 12 is constructed, for example, as a photomultiplier or as an APD, since the radiation intensities to be received are low. The amplifier 13 is constructed as a lock-in amplifier and is connected both to the detector 12 and to the laser 4. The laser 4 is equipped internally with a pulse selector 18 for generation of variable time intervals between successive laser pulses. The control unit 14 can adjust the time intervals via corresponding control signals. The optical phase delay system 9 has the effect in this context of a defined change in the polarisation direction of the radiation passing through.

For the functioning of the confocal detection, reference is made to WO2009/146906 A2, the disclosure content of which is incorporated here as far as possible. Since a significantly increased backscatter occurs at interfaces, the control unit 14 can determine the position and shape of interfaces from the intensities detected with a low outlay. When measurement of the potential treatment area, limited for example to physiologically still appropriate dimensions, is complete, the control unit 14 can identify the various interfaces within each x-z plane or y-z plane, for example by simple serial numbering from the front (interface with the shortest distance from the focussing lens system 8 in the z direction) towards the back (interface with the longest distance from the focussing lens system 8 in the z direction). With the aid of, for example, three or more points per interface, the control unit can fit, for example, a model of the eye lens with respect to a minimal deviation from the measurement values. The model then represents the shape and position of the interfaces measured.

The model determined can be updated during the treatment, for example in order to take into account changes in the position of the ocular tissue due to any eye movements occurring during the treatment. For this, the attenuator 12 is temporarily folded back into the illumination beam path B. The irradiation control data which have not yet been transmitted into the ocular tissue are then expediently re-determined with the aid of the updated model.

Figure 10:
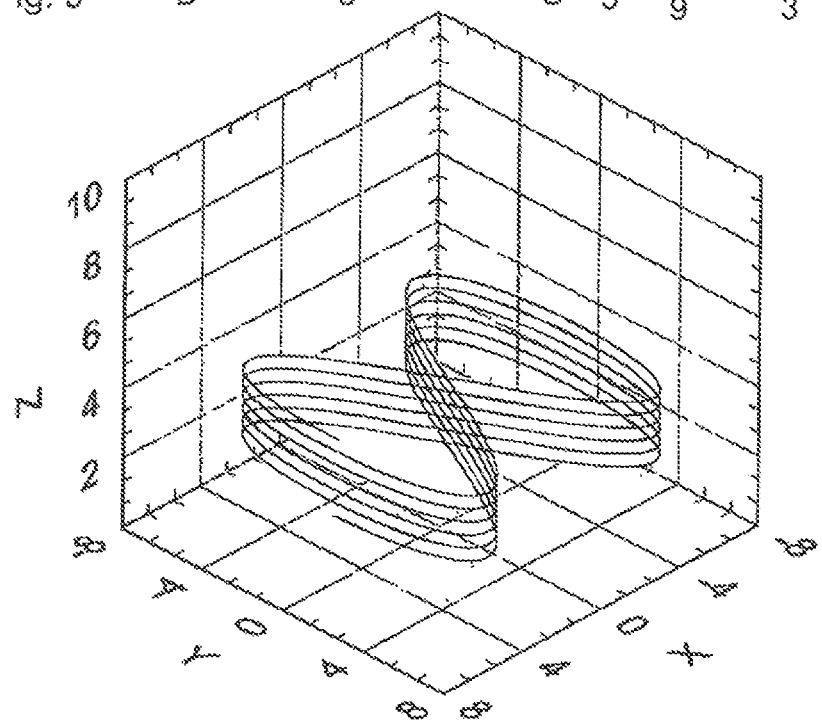
FIG. 10 shows scanning curve for confocal measurement of interfaces in the eye.

FIG. 10 shows an exemplary scanning curve for the confocal detection in the form of spatially displaced figure-of-eight curves, which can be realised as a Lissajous figure by means of the scanning unit 7 and z focussing. It has the advantage that representative data for the reconstruction of an interface model (or a model of the cornea) can be determined with a high accuracy in a short time.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE SYMBOLS 1 ophthalmologic laser device
2 eye
2.1 cornea
2.2 iris
2.3 vitreous body
2.4 retina
3 eye lens
3.1 embryonic nucleus
3.2 foetal nucleus
3.3 adult nucleus
3.4 cortex
3.5 equatorial nucleus arc
3.6 capsular bag
3.6A anterior membrane
3.6B posterior membrane
3.6C equator
3.8 zonular lamella
3.9 zonular fibre
3.10 lens epithelial cells
4 pulsed laser
5 beam splitter
5' polarisation beam splitter
6 scanning lens system
7 scanner unit
8 focussing lens system
9 optical phase delay system
10 deflector mirror
11 confocal aperture
12 OCT
12' detector
13 amplifier
14 control unit
15 attenuator
16 modulator
17 fixing device
17.1 suction device
17.2 interruption
17.3 disc
17.4 recess
18 pulse selector
B treatment beam path
D detection beam path
L light
V target volume
IOL intraocular lens
H haptics
K capsulotomy opening
Z circulation opening

What is claimed is:

1. An ophthalmologic laser device comprising:
a pulsed laser configured to produce treatment laser pulses of a predetermined pulse energy that propagate along a treatment beam path;
a focusing lens system disposed in the treatment beam path;
a variably adjustable beam deflector unit disposed in the treatment beam path and configured to deflect the treatment laser pulses to different volumes;
a measuring equipment configured to determine a shape and position of optical interfaces along a detection beam path; and
a controller configured to control the pulsed laser and the variably adjustable beam deflector unit, the controller being configured to:
determine, using the measuring equipment, a shape and position of at least one interface of a membrane of a capsular bag of an eye located in a treatment area,
determine, based on the predetermined pulse energy, an effect distance over which a hypothetical pressure wave, which would be induced by irradiation of tissue in an interior space of the capsular bag of the eye with a laser pulse of the predetermined pulse energy, must propagate before an intensity of the hypothetical pressure wave has decreased to a level insufficient to tear the membrane of the capsular bag of the eye but sufficient to cause a photodisruption-free, non-linear interaction with the membrane that detaches cells or molecules from the membrane or deactivates the cells or molecules,
determine, as a function of the effect distance, coordinates of a center of a target volume, the center of the target volume being located at the effect distance from the at least one interface of the membrane of the capsular bag of the eye, and
adjust the deflector unit so as to deflect the treatment laser pulses produced by the pulsed lasr to the target volume.

2. The laser device according to claim 1, wherein the control unit determines the coordinates of the center of the target volume such that the target volume lies completely in an interior space of the capsular bag.

3. The laser device according to claim 1, wherein the effect distance is determined using at least one of a sample calculation or a look-up table.

4. The laser device according to claim 1, further comprising a fixing device for releasable fixing of a position of the eye relative to the focusing lens system,
wherein the control unit is further configured to fix, using the fixing device, the eye before determining the shape and position of the at least one interface of the membrane of the capsular bag of the eye, and
wherein the control unit is further configured to release the eye after deflecting the treatment laser pulses produced by the pulsed laser to the target volume.

5. The laser device according to claim 4, wherein the control unit is further configured to, after the fixing the eye and before releasing the eye, at least one of the following additional incisions using the pulsed laser or an additional laser:
capsulorhexis incisions in an anterior capsular bag membrane,
fragmentation incisions in a lens of the eye,
corneal access incisions, and
limbal relaxing incisions.

6. The laser device according to claim 1, wherein the treatment beam path runs as a free beam through a cornea of the eye and a pupil of the eye.

7. The laser device according to claim 1, comprising an ultra-short pulse laser and a short pulse laser, wherein the beams of these two lasers run partially coaxially in the treatment beam path.

8. The laser device according to claim 1, wherein the device is switchable between an emission with image-recording radiation output and an emission with treatment radiation output, and wherein the control unit is configured to implement:
adjustment of the emission with image-recording radiation output for determination of the shape and position of the at least one interface, and
adjustment of the emission with treatment radiation output for irradiation of the target volume or several target volumes.

* * * * *